(12) United States Patent
Hu et al.

(10) Patent No.: US 10,663,316 B2
(45) Date of Patent: May 26, 2020

(54) NAVIGATION DEVICE AND METHOD (71) Applicant: BOE TECHNOLOGY GROUP CO., LTD., Beijing (CN)

(72) Inventors: Yong Hu, Beijing (CN); Long Wang, Beijing (CN); Ken Wen, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 24 days.

(21) Appl. No.: 15/554,940

(22) PCT Filed: Feb. 21, 2017

(86) PCT No.: PCT/CN2017/074283
§ 371 (c)(1),
(2) Date: Aug. 31, 2017

(87) PCT Pub. No.: WO2017/202081
PCT Pub. Date: Nov. 30, 2017

(65) Prior Publication Data
US 2018/0106636 A1    Apr. 19, 2018

(30) Foreign Application Priority Data
May 23, 2016 (CN) .......................... 2016 1 0345176

(51) Int. Cl.
*G01C 21/36* (2006.01)
*A61H 3/06* (2006.01)
(Continued)

(52) U.S. Cl.
CPC ......... *G01C 21/3652* (2013.01); *A61H 3/061* (2013.01); *G01C 21/20* (2013.01);
(Continued)

(58) Field of Classification Search
CPC ................ G01C 21/20; G01C 21/3652; G01C 21/2691; A61H 3/061
See application file for complete search history.

(56) References Cited

U.S. PATENT DOCUMENTS 10,210,723 B2 * 2/2019 Mappus .................. G08B 6/00
2006/0184318 A1    8/2006 Yoshimine
(Continued)

FOREIGN PATENT DOCUMENTS

CN          1813169 A      8/2006
CN       202069017 U      12/2011
(Continued)

OTHER PUBLICATIONS

International Search Report of PCT/CN2017/074283 in Chinese, dated Apr. 21, 2017 with English translation.
(Continued)

*Primary Examiner* — Donald J Wallace
(74) *Attorney, Agent, or Firm* — Collard & Roe, P.C.

(57) ABSTRACT

A wearable tactile navigation device and method. The wearable tactile navigation device includes a tactile navigation actuator. The tactile navigation actuator includes a feedback contact and is configured to control the feedback contact based on a direction indication signal to generate a tactile signal having a direction indication. A direction indicated by the tactile signal substantially coincides with a suggested moving direction provided to a user of the wearable tactile navigation device.

20 Claims, 8 Drawing Sheets

(51) Int. Cl.
*G01C 21/20* (2006.01)
*A61B 5/00* (2006.01)

(52) U.S. Cl.
CPC ............ *G01C 21/3691* (2013.01); *A61B 5/00* (2013.01); *A61H 2003/063* (2013.01); *A61H 2201/165* (2013.01); *A61H 2201/5058* (2013.01)

(56) References Cited

U.S. PATENT DOCUMENTS

| | | | | |
|---|---|---|---|---|
| 2013/0218456 | A1* | 8/2013 | Zelek | G01C 21/3652 701/412 |
| 2014/0180582 | A1* | 6/2014 | Pontarelli | G08B 6/00 701/494 |
| 2015/0049325 | A1* | 2/2015 | Curtis | G01S 17/93 356/4.01 |
| 2015/0198454 | A1* | 7/2015 | Moore | H04N 13/204 701/428 |
| 2015/0294597 | A1 | 10/2015 | Rizzo | |
| 2016/0077202 | A1* | 3/2016 | Hirvonen | G01S 13/90 342/25 R |
| 2016/0317383 | A1 | 11/2016 | Stanfield et al. | |
| 2017/0224573 | A1* | 8/2017 | Challa | A45B 9/04 |

FOREIGN PATENT DOCUMENTS

| | | |
|---|---|---|
| CN | 105115493 A | 12/2015 |
| CN | 205126750 U | 4/2016 |
| CN | 105547318 A | 5/2016 |
| CN | 105748265 A | 7/2016 |
| GB | 2527139 A | 12/2015 |
| JP | 2008-286546 A | 11/2008 |
| WO | 2007/105937 A1 | 9/2007 |
| WO | 2012/159128 A2 | 11/2012 |
| WO | 2014/066516 A1 | 5/2014 |
| WO | 2015/100482 A1 | 7/2015 |

OTHER PUBLICATIONS

Notice of Transmittal of the International Search Report of PCT/CN2017/074283 in Chinese, dated Apr. 21, 2017.
Written Opinion of the International Searching Authority of PCT/CN2017/074283 in Chinese, dated Apr. 21, 2017 with English translation.
Chinese Office Action in Chinese Application No. 201610345176.X, dated May 2, 2017 with English translation.
Second Chinese Office Action in Chinese Application No. 201610345176.X, dated Jan. 24, 2018 with English translation.
Partial Supplementary European Search Report in EP Application No. 17757657.6 dated Dec. 18, 2019.

* cited by examiner

NAVIGATION DEVICE AND METHOD

CROSS REFERENCE TO RELATED APPLICATIONS

This application is the National Stage of PCT/CN2017/074283 filed on Feb. 21, 2017, which claims priority under 35 U.S.C. § 119 of Chinese Application No. 201610345176.X filed on May 23, 2016, the disclosure of which is incorporated by reference.

TECHNICAL FIELD

Embodiments of the present disclosure relate to a field of navigation technologies, and more particularly, to a wearable tactile navigation device and method.

BACKGROUND

A visually impaired person, in a travelling process, cannot conduct a comprehensive judgment on directions and traffic information by visual sense. An existing solution that assists the visually impaired person in travelling by an intelligent hardware device includes converting visual information into auditory or other sensory information. For example, feedback information such as a voice prompt or voice navigation can be provided to the visually impaired person. However, problems in the existing solution may include: for example, the voice prompt or the voice navigation and other feedback information may not be intuitive enough, and when the visually impaired person receives the feedback information, he/she needs to perform corresponding interpretation on the feedback information according to a current situation, so as to derive an indicative result such as a moving direction or whether or not to take moving actions.

In addition, a current navigation device generally provides map navigation (including visual navigation or voice navigation) on an intelligent terminal. These navigation devices require a user to conduct the comprehensive judgment by himself/herself with reference to a map.

SUMMARY

Embodiments of the disclosure provide a wearable tactile navigation device, comprising: a tactile navigation actuator, including a feedback contact and configured to control the feedback contact based on a direction indication signal to generate a tactile signal having a direction indication, where a direction indicated by the tactile signal substantially coincides with a suggested moving direction provided to a user of the wearable tactile navigation device.

For example, the tactile navigation actuator includes a plurality of feedback contacts, and each feedback contact corresponds to a direction indication action region.

For example, the tactile navigation actuator sequentially controls the plurality of feedback contacts in a certain order to generate the tactile signal based on the direction indication signal.

For example, a size of the tactile signal changes based on an indication urgency degree of the direction indication signal.

For example, the tactile signal includes at least one of a force signal, a temperature signal, and an electrical signal.

For example, the tactile signal includes a force signal, and an implementation mode in which a single feedback contact generates the force signal includes vibrating, tapping or pressing.

For example, the wearable tactile navigation device further comprises a motion sensor, where the motion sensor is configured to detect a twisting direction of the tactile navigation actuator, and the twisting direction of the tactile navigation actuator is used for assisting generation of the direction indication signal.

For example, the wearable tactile navigation device comprises a wearable vest, a wristband, an arm band, a knee pad, a belt, a headband, a glove or a hat.

For example, the wearable tactile navigation device is a wearable vest, and the feedback contacts at least includes a first feedback contact located at a left shoulder of the vest and a second feedback contact located at a right shoulder of the vest, and a direction indication action region corresponding to the first feedback contact is a left half of a body of the user, and a direction indication action region corresponding to the second feedback contact is a right half of the body of the user.

For example, the wearable tactile navigation device further comprises:

an environment detector, configured to detect current environment information of the user;

a locator, configured to detect a current location of the user and to acquire map information;

an inputter, configured to receive destination information input by the user; and a processor, configured to compute a navigation route according to the destination, the current location of the user and the map information, and to generate the direction indication signal based on the navigation route and the current environment information of the user detected by the environment detector.

For example, the processor is further configured to:

determine a direction toward which the user substantially faces after moving based on a location before and a location after the user moves toward a certain direction; or determine a current direction toward which the user approximately faces based on different orientations of two or more feedback contacts provided in the tactile navigation actuator.

Embodiments of the disclosure provide a wearable tactile navigation method, comprising:

receiving a direction indication signal; and generating a tactile signal having a direction indication based on the direction indication signal, wherein a direction indicated by the tactile signal substantially coincides with a suggested moving direction provided to a receiver of the tactile signal.

For example, a size of the tactile signal changes based on an indication urgency degree of the direction indication signal.

For example, the wearable tactile navigation method further comprises:

acquiring current map information;

detecting a current location of the receiver of the tactile signal;

receiving a destination input by the receiver of the tactile signal;

computing a navigation route based on the destination, the current location of the receiver of the tactile signal, and the acquired map information;

detecting current environment information of the receiver of the tactile signal; and generating the direction indication signal based on the navigation route and the current environment information of the receiver of the tactile signal.

For example, the tactile signal includes a plurality of tactile sub-signals, each tactile sub-signal corresponds to a direction indication action region;

the tactile sub-signals are sequentially generated in a certain order based on the direction indicated by the tactile signal.

For example, the wearable tactile navigation method further comprises: determining a current direction toward which the receiver of the tactile signal substantially faces, including:

determining the current direction toward which the receiver of the tactile signal substantially faces based on a location before and a location after the receiver of the tactile signal moves toward a certain direction; or determining the current direction toward which the receiver of the tactile signal substantially faces based on different locations of two or more direction indication action regions.

For example, the wearable tactile navigation method further comprises:

detecting a twisting direction of a direction indication action region with respect to the current direction toward which the receiver of the tactile signal substantially faces, the twisting direction being used for assisting generation of the direction indication signal.

BRIEF DESCRIPTION OF THE DRAWINGS

In order to illustrate the technical solutions in the embodiments of the present disclosure or the existing arts more clearly, the drawings need to be used in the description of the embodiments or the existing arts will be briefly described in the following; it is obvious that the drawings described below are only related to some embodiments of the present disclosure, for one ordinary skilled person in the art, other drawings can be obtained according to these drawings without making other inventive work.

DETAILED DESCRIPTION

Hereafter, the technical solutions of the embodiments of the present disclosure will be described in a clearly and fully understandable way in connection with the drawings related to the embodiments of the disclosure. It is obvious that the described embodiments are just a part but not all of the embodiments of the present disclosure. Based on embodiments of the present disclosure, all other embodiments obtained by those skilled in the art without making other inventive work should be within the scope of the present disclosure.

A wearable tactile navigation device and method provided by embodiments of the present disclosure can provide a user (e.g., a visually impaired person, a non-visually impaired person with a weak direction sense or other persons who needs travelling route navigation) with a directional tactile navigation signal, thereby providing more direct navigation advice than navigation information such as a voice prompt, etc. Hereinafter, a wearable tactile navigation device and method provided by an embodiment of the present disclosure will be illustrated in details in conjunction with the drawings.

Figure 1A:
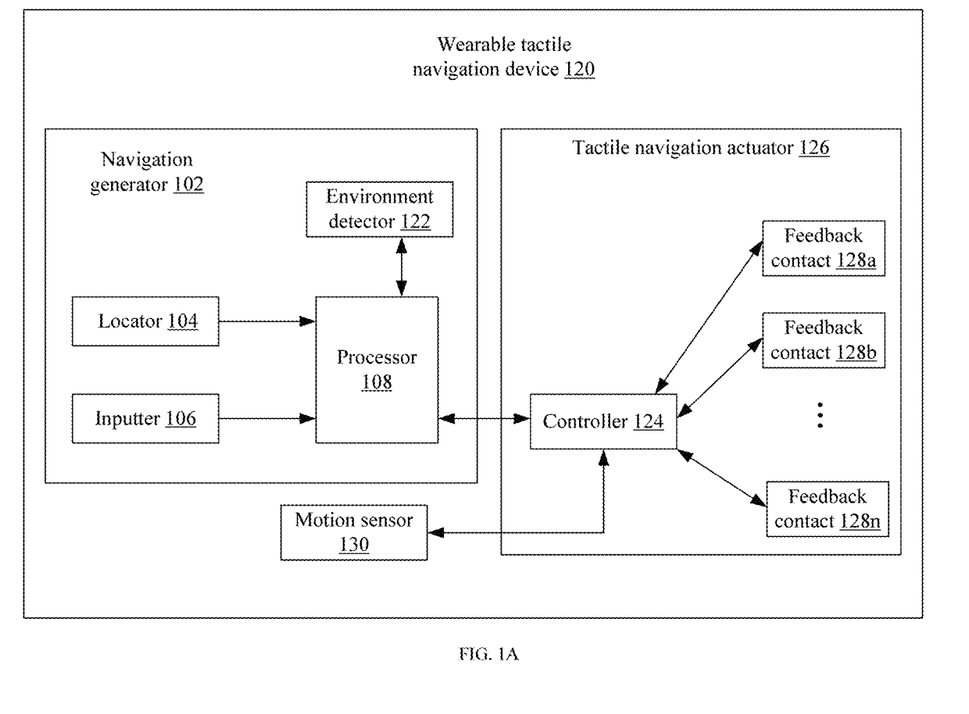
FIG. 1A is a first structural schematic diagram of a wearable tactile navigation device provided by an embodiment of the present disclosure.

With reference to FIG. 1A, an embodiment of the present disclosure provides a wearable tactile navigation device 120. The wearable tactile navigation device 120 comprises a tactile navigation actuator 126. The tactile navigation actuator 126 includes a feedback contact, configured to control the feedback contact according to a direction indication signal to generate a tactile signal having a direction indication, where a direction indicated by the tactile signal substantially coincides with a suggested moving direction provided to the user of the wearable tactile navigation device. For example, the tactile navigation actuator 126 includes a plurality of feedback contacts, each feedback contact corresponding to a direction indication action region. The tactile navigation actuator 126 sequentially controls the plurality of feedback contacts in a certain order to generate the tactile signal according to the direction indication signal, where the tactile signal may change according to an indication urgency degree of the direction indication signal. The tactile signal includes at least one of a force signal, a temperature signal, and/or an electrical signal. When the tactile signal is the force signal, an implementation mode in which a feedback contact generates the force signal includes vibrating, tapping or pressing.

It should be noted that, in embodiments of the present disclosure, the term "substantially" indicates that an error between a desired value and an actual value does not exceed a preset range. The preset range may be within ±5%, ±10% or another suitable range. For example, an expression "a direction indicated by the tactile signal substantially coinciding with a suggested moving direction provided to the user of the wearable tactile navigation device" may indicate that an error range between an angle of the direction indicated by the tactile signal and an angle of a suggested moving direction provided to the user does not exceed the angle of the suggested moving direction provided to the user by ±5%, ±10% or another suitable error range.

The wearable tactile navigation device 120 may further comprise a navigation generator 102. In some embodiments, the wearable tactile navigation device 120 may further comprise other components not shown in FIG. 1A, for example, a warning device (e.g., a lamp capable of automatically blinking when ambient light is insufficient or a loudspeaker for playing a voice prompt), a power supply (e.g., a button battery) and so on. In some examples, the navigation generator 102 may include a locator 104, an inputter 106, a motion sensor 130, an environment detector 122, and a processor 108. For example, the navigation generator 102 may be a mobile phone specialized for a blind person or another electronic device specialized for a blind person. Since the user may wear or carry the navigation generator 102, the locator 104 may be configured to detect a current location of the user and to acquire map information. For example, the locator 104 may be a Global Positioning System (GPS) sensor, for determining the current location of the user, and transmitting the determined location information to the processor 108. The locator 104 may also be another electronic device capable of determining the location of the user, for example, the Beidou satellite navigation system or the mobile base station locating system, which is not limited in the present disclosure.

The inputter 106 may be configured to receive destination information input by the user. For example, the inputter 106 may include a keyboard (e.g., a keyboard dedicated for a visually impaired person), so that the user may directly input the destination information through the keyboard. For another example, the inputter 106 may include a microphone, so that the user can input the destination information by voice. For another example, the inputter 106 may include other buttons, touch devices, and motion-sensing devices, so that the user can select the destination information that has been stored in the navigation generator 102. The inputter 106 transmits the destination information to the processor 108.

The processor 108 may be configured to compute a navigation route according to the current location of the user, the input destination information, and the stored map information. The navigation route may include one or more routes from the current location of the user to the destination, and the user may select one of the routes for navigation. In some examples, the processor 108 receives current environment information of the user (e.g., traffic information) from the environment detector 122, and generates direction indication information according to the navigation route and the current environment information of the user. The direction indication information may include real-time and step-by-step directional navigation information. For example, when the user walks along the navigation route toward the destination, the processor 108 may generate the direction indication information used for directing movement of the user in real time according to the navigation route (e.g., the direction indication information including indication information instructing the user to go forward, turn left and then continue to go forward, or turn right and then continue to go forward, etc). For example, when the current traffic information of the user indicates that a moving obstacle (e.g., a moving vehicle) appears in front, the processor 108 may generate real-time direction indication information for instructing the user to temporarily stop going forward; and after the environment detector 122 no longer detects the moving obstacle, the processor 108 may generate real-time direction indication information for instructing the user to continue to go forward. The processor 108 may transmit the generated direction indication information to the wearable tactile navigation device 120.

In some embodiments, the processor 108 firstly determines a current direction toward which the user approximately faces at a current time. For example, the navigation generator 102 or the wearable tactile navigation device 120 may include a motion-sensing device. When it is needed to determine the current direction toward which the user approximately faces, the wearable tactile navigation device 120 may instruct the user to wave an arm forward by a voice prompt, so that the motion-sensing device senses the arm waved by the user and transmits a sensing result to the processor 108. Thus, the processor 108 may determine the current direction toward which the user approximately faces according to the sensing result of the motion-sensing device. For another example, the wearable tactile navigation device 120 may instruct the user to move forward a few steps by a voice prompt, and thus, the motion sensor 130 (e.g., a gyroscope) can detect the current direction toward which the user approximately faces. Then, the processor 108 generates the direction indication information according to the navigation route, the current environment information of the user, and the current direction toward which the user approximately faces. For example, it is supposed that the user is standing on a sidewalk extending in a north-south direction, and the navigation route instructs to go north. Since the user is facing the east at a current moment, the processor 108 firstly generates direction indication information instructing the user to turn left by about 90 degrees, and then generates direction indication information instructing the user to go forward.

Figure 2A:
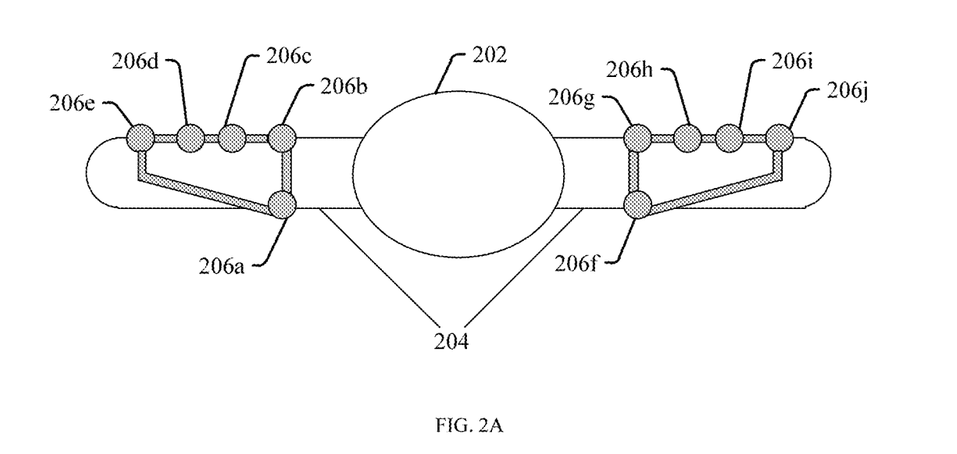
FIG. 2A is a schematic diagram of an example wearable tactile navigation device and its tactile navigation actuator provided by an embodiment of the present disclosure.

For example, in combination with the GPS, the wearable tactile navigation device 120 may determine the current direction toward which the user approximately faces according to different locations of two or more preset location reference points on the map. The preset location reference points may be located in different portions of the wearable tactile navigation device 120. For example, with respect to a navigation vest as shown in FIG. 2A, it is possible to provide location reference points in positions of the navigation vest that correspond to the abdomen and the back of the user.

For example, a controller 124 may receive the current direction toward which the user approximately faces determined by the processor, and the direction indication information may be generated according to the current direction toward which the user approximately faces. For example, the determining a current direction toward which the user approximately faces, includes: determining a direction toward which the user faces after moving according to a location before and a location after the user moves toward a certain direction; or, determining the current direction toward which the user approximately faces according to different orientations of two or more feedback contacts provided in the wearable navigation device.

The processor 108 may include a processor (or a microprocessor) and a memory. The processor may process a data signal, and may include various computational structures, for example, a complex instruction set computer (CISC) structure, a reduced instruction set computer (RISC) structure, or a structure that implements a variety of instruction set combinations. The memory may store instructions and/or data executed by the processor. These instructions and/or data may include code, for implementing some functions or all functions as described in the embodiments of the present disclosure. For example, the memory includes a dynamic random access memory (DRAM), a static random access memory (SRAM), a flash memory, an optical memory, or other memory known to those skilled in the art. In some embodiments, the processor 108 may be a dedicated hardware device, for example, a DSP, an ASIC, an FPGA, a circuit board, etc., for implementing some functions or all functions as described in the embodiments of the present disclosure.

Figure 1B:
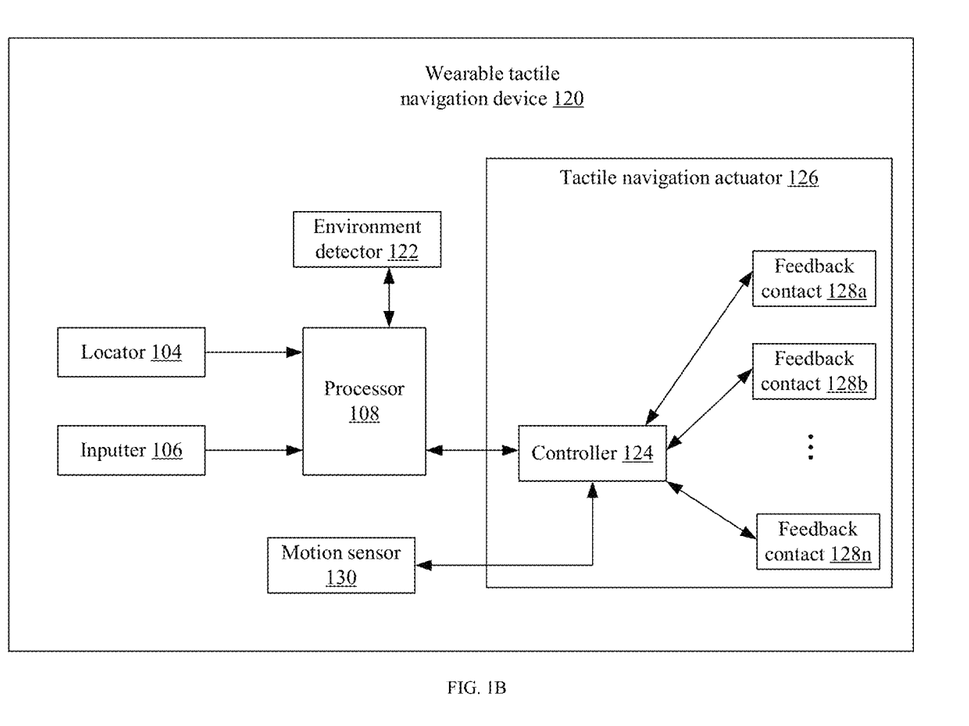
FIG. 1B is a second structural schematic diagram of a wearable tactile navigation device provided by an embodiment of the present disclosure.

The environment detector 122 may be configured to detect the current environment information of the user. For example, the environment detector 122 may detect traffic information around the user, including a static obstacle, a moving obstacle, a moving speed of the obstacle, an abnormal traffic condition, and possibility of passing a road, etc. For example, the environment detector 122 may also detect an indoor environment condition, for example, an exhibition hall, a conference hall, or other interior space, and an outdoor environment condition, e.g., a scenic spot, a street, a public square, or other outdoor spaces, and then generate corresponding environment information. The environment detector 122 may include a detection sensor, an image sensor (e.g., a micro camera or a camera), or other sensors. The environment detector 122 transmits the detected current traffic information of the user to the processor 108, so that the processor 108 may generate the direction indication information according to the current traffic information of the user. In FIG. 1A and FIG. 1B, the environment detector 122 is provided in the wearable tactile navigation device 120; and in some embodiments, the environment detector 122 may also be provided in the navigation generator 102.

The tactile navigation actuator 126 may include one or more of the controller 124 and the feedback contacts 128 (128a, 128b . . . 128n). The controller 124 may be configured to receive the direction indication signal and convert the direction indication signal into a feedback driving signal. The feedback driving signal may be used for driving the feedback contacts 128 (128a, 128b . . . 128n) to output a directional tactile signal. For example, the tactile navigation actuator 126 includes the feedback contacts 128 (128a, 128b . . . 128n), and the tactile navigation actuator 126 controls the feedback contacts 128 to generate the tactile signal according to the feedback driving signal. The tactile signal may include one or more of a force signal, a temperature signal, and an electrical signal.

For example, the controller 124 includes a driving motor for providing power, a microprocessor for controlling the driving motor and/or other relevant circuit components. The tactile navigation actuator 126 may be a flexible massage hand provided at the shoulder of the user, and a feedback contact 128 may be a finger (or a palm) contact point of the flexible massage hand. The controller 124 converts the received direction indication signal (e.g., a going-forward signal, a stop signal, or a signal of turning right by 60 degrees, etc.) into an electrical signal for driving the finger (or the palm) of the flexible massage hand to vibrate, to squeeze or to tap. When the finger (or the palm) of the flexible massage hand is vibrating, squeezing or tapping under an action of the electrical signal, the tactile navigation actuator 126 accordingly outputs a directional force signal to the user. A direction of the force signal substantially coincides with the suggested moving direction provided to the user. For example, when the suggested moving direction provided to the user is going forward, the direction of the force signal is pointed substantially forward with respect to the user; when the suggested moving direction provided to the user is turning right by 45 degrees, the direction of the force signal is pointed substantially 45 degrees to the right with respect to the user; and when the moving indication provided to the user is to stop, the direction of the force signal is pointed backward with respect to the user. An exemplary wearable tactile navigation device for outputting a directional force signal and its tactile navigation actuator will be described in details below in conjunction with FIG. 2A to FIG. 2D.

In some examples, the tactile navigation actuator 126 controls a plurality of feedback contacts 128 to generate the force signal of the tactile signal, each feedback contact including a preset direction indication action region. The force signal of the tactile signal may point to any direction, so that the user may be provided with different advises of direction navigation.

A force feedback implementation mode of the force signal of the tactile signal at a single feedback contact 128 includes vibrating, tapping, pressing, or squeezing, etc. For example, the force feedback implementation mode of each feedback contact 128 may include electromagnetic vibrating, tapping with a certain intermittent rhythm, piezoelectric pressure, or other implementation modes.

In some examples, the tactile signal may also include a temperature signal. For example, the controller 124 includes the processor (or the microprocessor) and/or other relevant circuit components, and the feedback contact 128 includes a material (e.g., a metal) that produces a temperature change according to a size of the applied electrical signal; the controller 124 converts the received direction indication signal into a feedback driving signal (e.g., an electrical signal) for controlling the feedback contacts 128 to produce the temperature change, and the tactile navigation actuator 128 sequentially applies the feedback driving signal to the feedback contacts 128 in a certain order to generate a temperature signal of the tactile signal. For example, when the respective feedback contacts 128 produce the temperature change under an action of the feedback driving signal, the tactile navigation actuator 126 accordingly outputs a directional temperature signal to the user. A direction indicated by the temperature signal coincides with the suggested moving direction provided to the user. An exemplary wearable tactile navigation device outputting a directional temperature signal and its tactile navigation actuator will be described in detail below in conjunction with FIG. 4A to FIG. 4C.

In some examples, a size of the tactile signal may change according to the indication urgency degree of the direction indication signal. For example, when an indication urgency degree of the direction indication signal is urgent, a size of a force in the tactile signal may be increased, and the temperature change produced by the temperature signal may also be increased. A size of the force in the tactile signal and/or the temperature change value may be divided into different levels according to the indication urgency degree of the direction indication signal, so that the higher the indication urgency degree of the direction indication signal is, the greater the size of the force in the tactile signal and/or the temperature change value are.

Figure 6A:
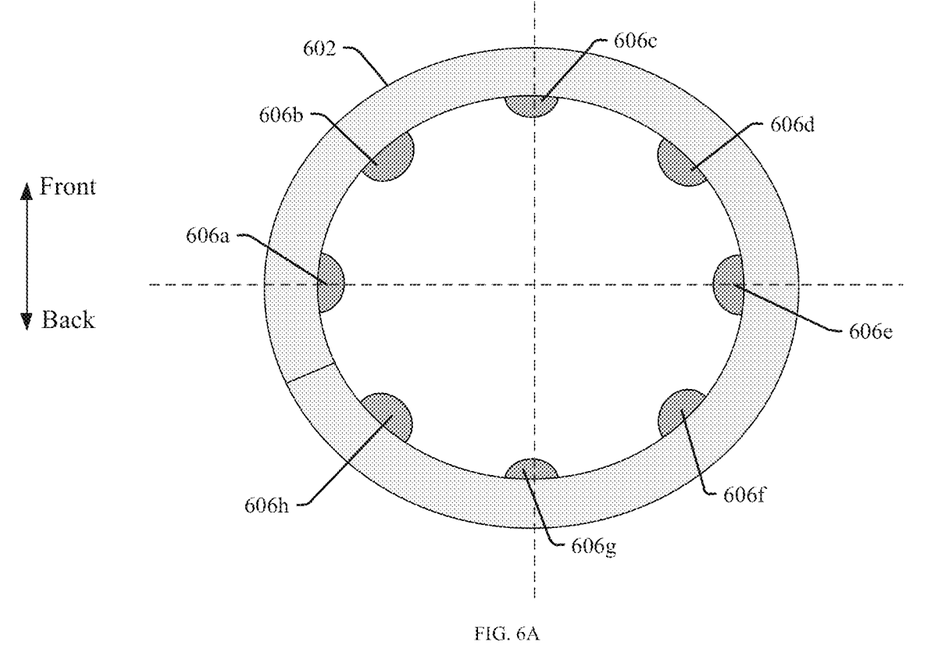
FIG. 6A to FIG. 6B are examples of updating setting of action regions corresponding to feedback points provided by an embodiment of the present disclosure.
Figure 6B:
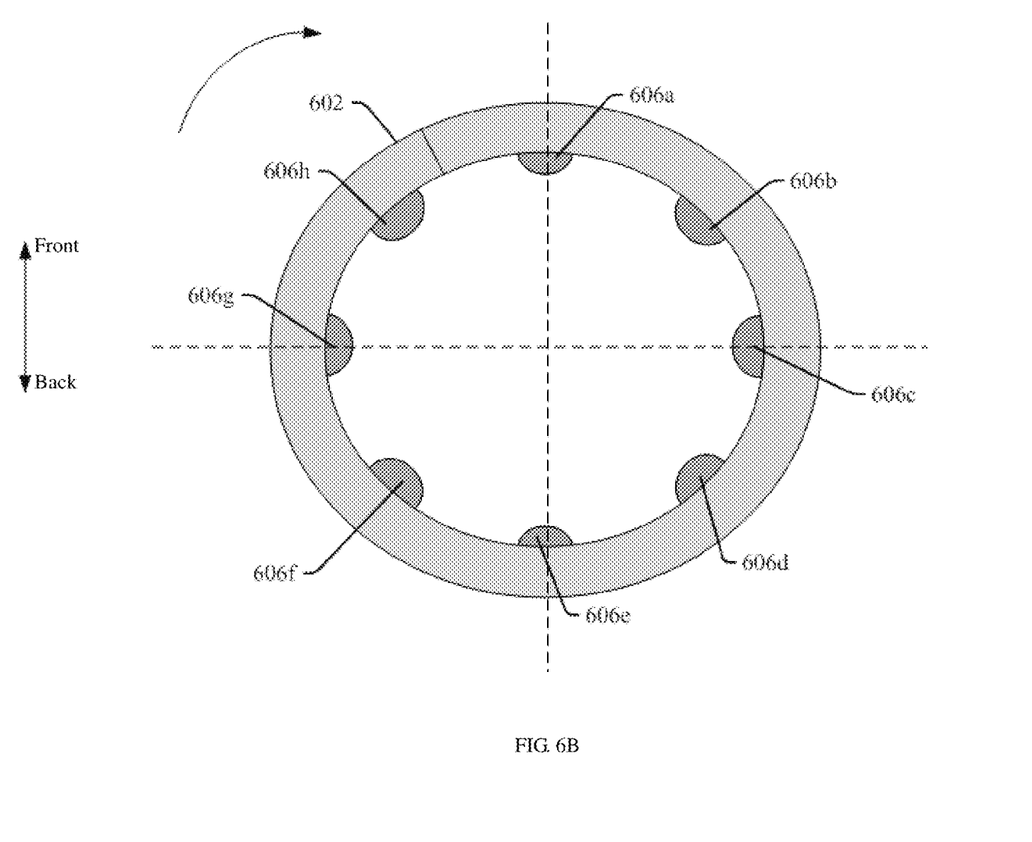

As shown in FIG. 1A, the wearable tactile navigation device 120 may further comprise a motion sensor 130. The motion sensor 130 may be configured to detect whether the tactile navigation actuator 126 is twisted or not and a direction after the twisting. For example, the motion sensor 130 is configured to detect the twisting direction of the tactile navigation actuator, the twisting direction of the tactile navigation actuator being used for assisting in generating the direction indication signal. The processor 108 may generate or update the direction indication signal according to the direction after the twisting of the tactile navigation actuator 126. For example, the wearable tactile navigation device 120 may be worn on the arm, the tactile navigation actuator 126 may be twisted as the arm moves, the motion sensor 130 may detect an angle or a direction of rotation of the tactile navigation actuator 126, and the processor 108 may generate or update in real time the direction indication signal according to the direction after the tactile navigation actuator 126 is rotated. Alternatively, the controller 124 may update the feedback driving signal according to the direction after the tactile navigation actuator 126 is twisted. FIG. 6A to FIG. 6B below will show an example of updating setting of the feedback driving signal. The motion sensor 130 may include an acceleration sensor, a gyroscope, or another sensor that detects motion. For example, the motion sensor 130 may include a multi-axis accelerometer, a multi-axis magnetometer, or a multi-axis gyroscope. The wearable tactile navigation device 120 provided by the embodiments of the present disclosure may be a vest, a wristband, an arm band, a knee pad, a belt, a headband, a glove, and a hat which are wearable. For example, when the wearable tactile navigation device 120 is a wearable vest, a feedback contact 128 may be provided at a location of a shoulder of the vest (e.g., the tactile navigation actuator 126 may be a massage hand, covering the shoulder of the user). For another example, when the wearable tactile navigation device 120 is a wearable wristband, a feedback contact 128 may be provided on an inner side of the wristband (e.g., when the user wears the wristband, the feedback contact may surround the wrist of the user, and may be in contact with the wrist of the user). The feedback contact 128 may be a regular or irregular spotty, blocky, planar, or linear contact point.

In some embodiments, the navigation generator 102 and the wearable tactile navigation device 120 may be different devices. For example, the wearable tactile navigation device 120 may be a vest, a wristband, an arm band, a knee pad, a belt, a headband, a hat or other wearable devices, and the navigation generator 102 may be a mobile phone dedicated for a visually impaired person or another electronic device dedicated for a visually impaired person. The tactile navigation provided by the embodiments of the present disclosure can be implemented by communication between the wearable tactile navigation device 120 and the navigation generator 102. In other embodiments, the navigation generator 102 and the wearable tactile navigation device 120 are a same integrated device. For example, the locator 104 (e.g., the GPS), the inputter 106 (e.g., an input keyboard or the microphone) and the processor 108 (e.g., the microprocessor) or other modules of the navigation generator 102 may be integrated into the vest, the wristband, the arm band, the knee pad, the belt, the headband, the hat or another wearable device which serves as the wearable tactile navigation device 120.

FIG. 1B shows another structural schematic diagram of the wearable tactile navigation device 120. The wearable tactile navigation device 120 may comprise the locator 104, the inputter 106, the processor 108, the environment detector 122, the motion sensor 130, and the tactile navigation actuator 126. The tactile navigation actuator 126 may include the controller 124 and the feedback contacts 128a, 128b . . . 128n. Functions and structures of respective devices (e.g., the locator 104, the inputter 106, the processor 108, the environment detector 122, the motion sensor 130, and the tactile navigation actuator 126) in FIG. 1B are similar or identical to functions and structures of similar devices in FIG. 1A, which will not be repeated here.

FIG. 2A shows an exemplary wearable tactile navigation device and its tactile navigation actuator. The wearable tactile navigation device may be a wearable smart vest. A mobile phone dedicated to a blind person may be taken as a control terminal (or the navigation generator) connected with the smart vest. The tactile navigation actuator may be a flexible massage hand provided at a location of the shoulder of the vest; each feedback contact may be a finger contact point, a palm contact point or another regular or irregular spotty, blocky, linear, or planar contact point. After the user inputs the destination through the mobile phone, it is possible to compute the navigation route according to the map information stored in the mobile phone and the GPS positioning device, and it is also possible to detect a surrounding environment condition (e.g., a traffic condition in front) through the environment detector (for example, a detection sensor) provided on the vest, and transmit an environment detection result to the mobile phone serving as the control terminal. The processor in the mobile phone computes a suggested going-forward direction according to the navigation route and the environment detection result, and transmits the going-forward direction as the direction indication signal to the controller (for example, the driving motor) provided within the vest. The controller generates a corresponding electrical signal to respectively drive the feedback contacts of the massage hands to impose a force with an appropriate size to the user.

In some embodiments, the feedback contacts include a first feedback contact located at the left shoulder of the vest and a second feedback contact located at the right shoulder of the vest. A direction indication action region corresponding to the first feedback contact located at the left shoulder is the left half of the body of the user, and a direction indication action region corresponding to the second feedback contact located at the right shoulder is the right half of the body of the user.

FIG. 2A shows a top view of the feedback contacts 206 provided at the location of the shoulders of the vest. On both sides of the head 202, the flexible massage hands cover on the shoulders 204 of the user, where the feedback contacts 206a and 206f (similar to thumbs of human hands) are both located on the back side, the feedback contacts 206b, 206c, 206d and 206e (similar to four fingers of the left hand) as well as the feedback contacts 206g, 206h, 206i and 206j (similar to four fingers of the right hand) are located on the chest side. The controller may generates the corresponding electrical signals to respectively control the respective feedback contacts 206a to 206j according to the direction indication signal, so that the feedback contacts 206a to 206j can apply the force signal to the user. The respective feedback contacts 206a to 206j can separately control a respective force being applied to the user, and the force signal may be a combination of forces separately applied to the user by the respective feedback contacts 206a to 206j.

Figure 2B:
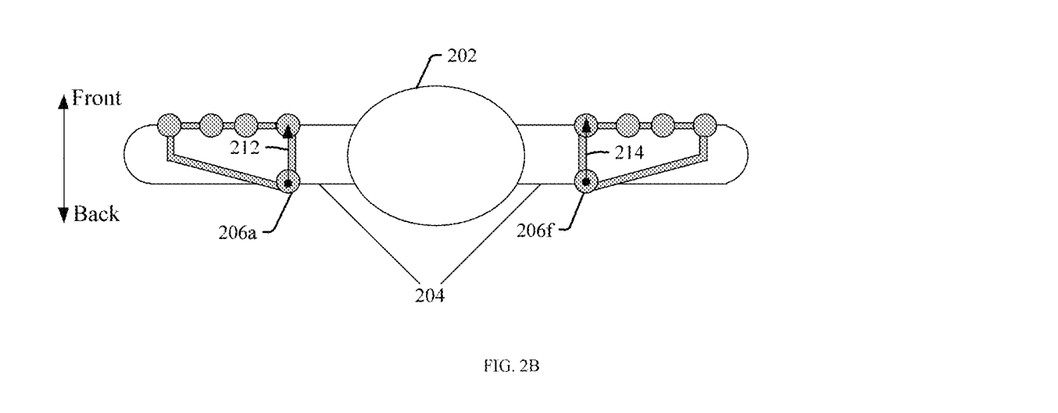
FIG. 2B to FIG. 2D are respectively schematic diagrams of force signals in different tactile signals provided by the tactile navigation actuator in FIG. 2A.

FIG. 2B shows a schematic diagram of a force signal of going forward provided by the tactile navigation actuator in FIG. 2A. For example, when the received direction indication signal is an indication signal instructing going forward, the controller may control the respective feedback contacts to apply forces to the user, so that the direction of the force signal received by the user is straight forward. In conjunction with an example of FIG. 2B, the controller may control the feedback contacts 206a and 206f to apply forces 212 and 214 to the user, where the direction indication action region of the feedback contact 206a is the left half of the body, the direction indication action region of the feedback contact 206f is the right half of the body, and the two feedback contacts 206a and 206f simultaneously apply forces straight forward to prompt the user to go straight forward.

Figure 2C:
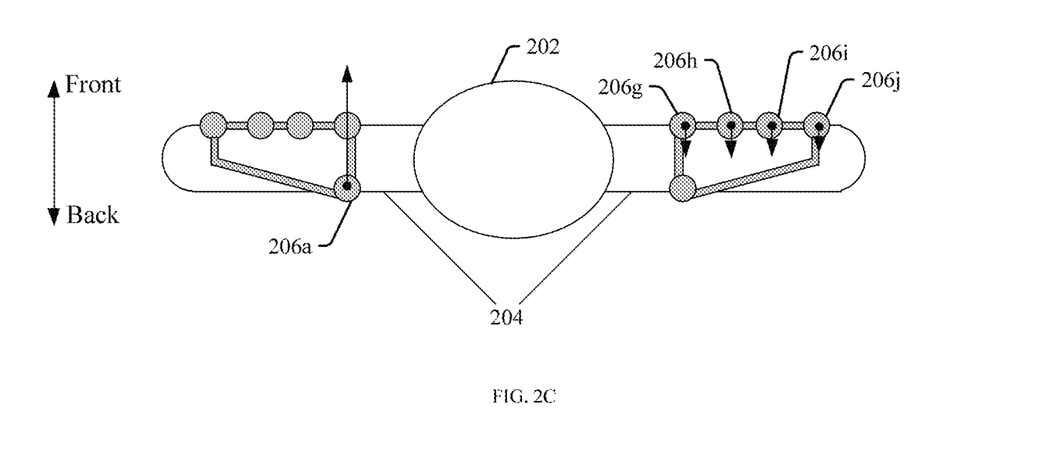

FIG. 2C shows a schematic diagram of a force signal of going forward in a direction of 45 degrees on the right provided by the tactile navigation actuator in FIG. 2A. For example, when the received direction indication signal is an indication signal instructing going forward in the direction of 45 degrees on the right, the controller may control the respective feedback contacts to apply forces to the user, to prompt the user to turn right. Next, when the user turns to a corresponding direction, the controller may again control the respective feedback contacts to apply forces to the user, so that the direction of the force signal received by the user is straight forward. The force signal acts on the user, prompting the user to go forward. Therefore, the user may achieve going forward in the direction of about 45 degrees on the right in two steps. In conjunction with an example of FIG. 2C, the controller may control the feedback contact 206*a* to apply a forward force to the user, and control the feedback contacts 206*g*, 206*h*, 206*i*, and 206*j* to apply a respective backward force to the user. Since the direction indication action region of the feedback contact 206*a* is the left half of the body of the user, the left half of the body of the user receives the forward force; and the direction indication action region of the feedback contacts 206*g*, 206*h*, 206*i*, and 206*j* is the right half of the body, the right half of the body of the user receives the backward forces. The feedback contacts 206*a*, 206*g*, 206*h*, 206*i*, and 206*j* simultaneously act on the user, to prompt the user to turn to a direction on the right side. When the user turns to the corresponding direction, the controller may control the feedback contacts 206*a* and 206*f* to apply forces to the user (as shown in FIG. 2B), where the indication action region of the feedback contact 206*a* is the left half of the body, the indication action region of the feedback contact 206*f* is the right half of the body, and the two feedback contacts 206*a* and 206*f* simultaneously apply forces straight forward, prompting the user to go straight forward. Therefore, the user may achieve going forward in the direction of about 45 degrees on the right in two steps.

Figure 2D:
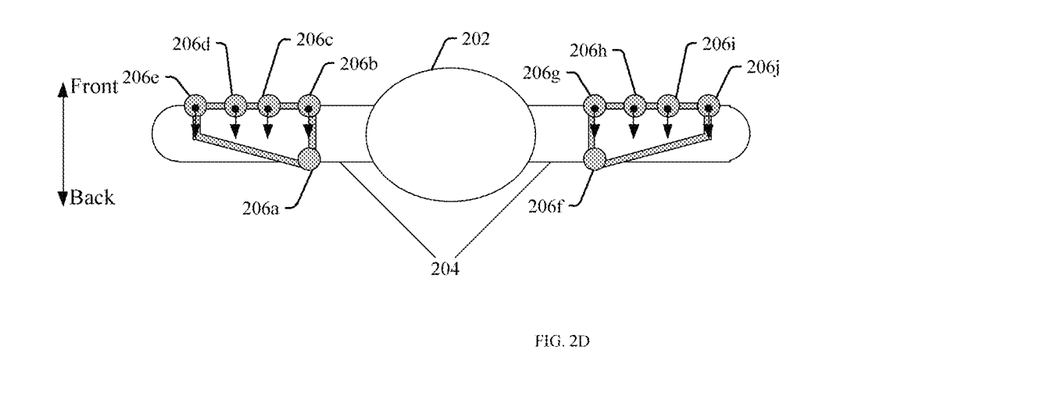

FIG. 2D shows a schematic diagram of a force signal of pausing movement provided by the tactile navigation actuator in FIG. 2A. For example, when the received direction indication signal is an indication signal instructing pausing movement (for example, there is an abnormal traffic condition, e.g., an obstacle, a channel, etc., in the straight front, and it is needed to temporarily stop walking), the controller may control the respective feedback contacts to apply forces to the user, so that the direction of the force signal received by the user is straight backward. In conjunction with an example of FIG. 2D, the controller may control the forces applied by the respective feedback contacts 206*b* to 206*e* and 206*g* to 206*j*, so that the direction of the force signal received by the user is directed straight backward, prompting the user to temporarily stop walking.

Figure 3:
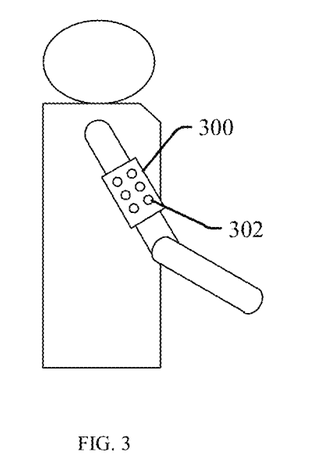
FIG. 3 is a schematic diagram of another example wearable tactile navigation device and its tactile navigation actuator provided by an embodiment of the present disclosure.

FIG. 3 shows another exemplary wearable tactile navigation device 300 and feedback contacts 302 in its tactile navigation actuator. The wearable tactile navigation device 300 may be worn on the arm or the wrist. For example, the wearable tactile navigation device 300 may be a wristband or an arm band. Each feedback contact 302 may be a spotty contact point as shown in FIG. 3, or may also be a blocky, planar, linear, or another shape of a contact point. The wearable tactile navigation device 300 may include a motion sensor for detecting a twisting direction of the arm, so that an output tactile signal (e.g., the force signal and/or the temperature signal) may be adjusted in real time according to the direction of the arm twisting, so that the direction indicated by the tactile signal substantially coincides with the suggested moving direction provided to the user at all times.

Figure 4A:
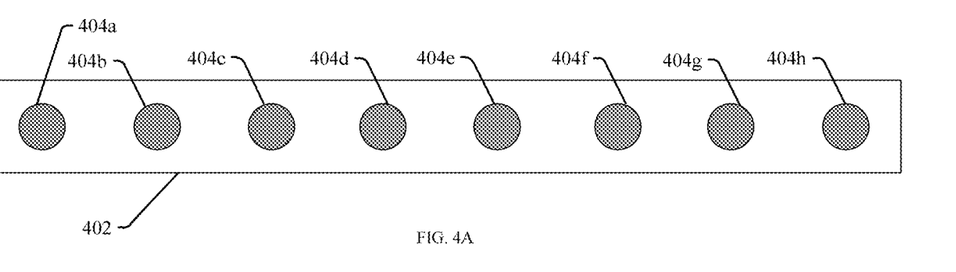
FIG. 4A is a schematic diagram of yet another example wearable tactile navigation device and its tactile navigation actuator provided by an embodiment of the present disclosure.
Figure 4B:
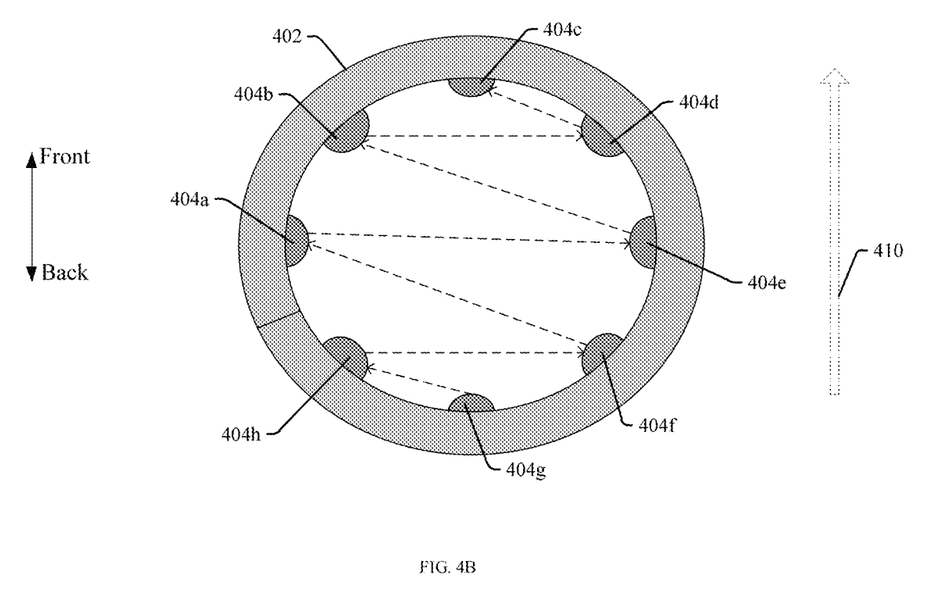
FIG. 4B and FIG. 4C are respectively schematic diagrams illustrating generation of temperature signals in different tactile signals provided by the tactile navigation actuator in FIG. 4A.
Figure 4C:
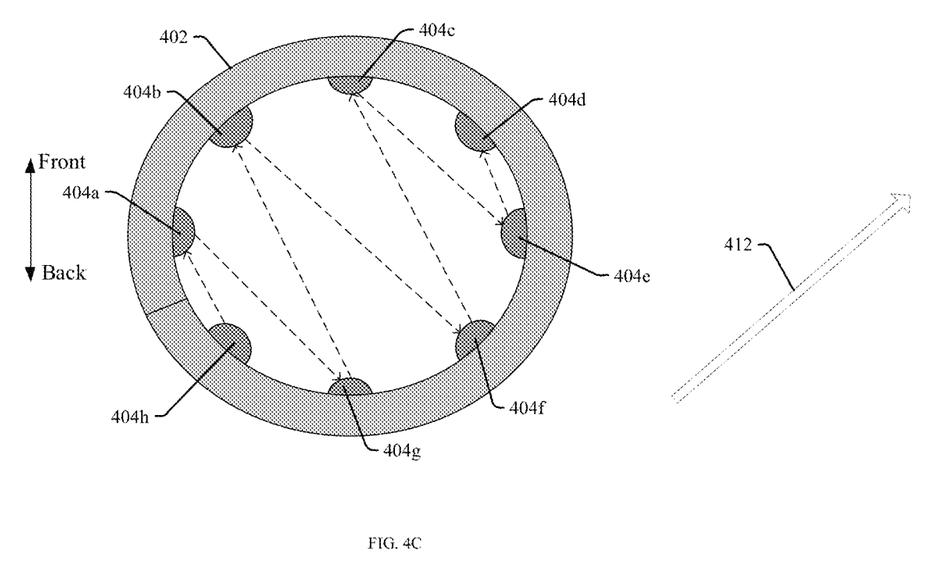

FIG. 4A shows another exemplary wearable tactile navigation device 402 and feedback contacts 404 (e.g., 404*a* to 404*h*) in its tactile navigation actuator. The wearable tactile navigation device 402 may be a wearable smart wristband, and the navigation generator (e.g., a blind dedicated mobile phone) is connected with the smart wristband. Each feedback contact 404 includes a material (e.g., a metal or other material capable of conducting heat or generating heat) whose temperature changes according to a size of the applied electrical signal. Each feedback contact 404 may be a regular or irregular potty, blocky, or planar contact point. After the user inputs the destination through the mobile phone, it is possible to compute the navigation route according to the map information stored in the mobile phone or downloaded in real time from a network and the GPS positioning device. It is also possible to detect a traffic condition in front through the environment detector (for example, the detection sensor) provided on the smart wristband, and transmit a traffic condition detection result to the mobile phone serving as the control terminal. The processor in the mobile phone computes a moving direction provided to the user according to the navigation route and the traffic condition detection result, and transmits the moving direction as the direction indication signal to the controller provided on the smart wristband. The controller generates a corresponding feedback driving signal (e.g., an electrical signal) to respectively control the feedback contacts 404 to produce a temperature change. For example, the controller may respectively apply the feedback driving signal to different feedback contacts 404 in a certain order and/or with a certain frequency (or at a certain time interval), resulting in the respective feedback contacts 404 producing the temperature change in a certain order and/or with a certain frequency (or at a certain time interval) under an action of the feedback driving signal. Thus, the wearable tactile navigation device accordingly outputs a directional temperature signal to the user. A direction indicated by the temperature signal substantially coincides with a suggested moving direction provided to the user. The time interval may be 1 second, 2 seconds, or another suitable time interval. As shown in FIG. 4B and FIG. 4C, the controller may determine the order according to the suggested moving direction provided to the user.

For example, as shown in FIG. 4B, the feedback contact 404*c* and the feedback contact 404*g* are respectively a foremost feedback contact and a hindmost feedback contact. When the suggested moving direction provided to the user is straight front, the controller may sequentially apply a driving electrical signal to the feedback contacts 404*g*, 404*h*, 404*f*, 404*a*, 404*e*, 404*b*, 404*d* and 404*c* according to an order shown by a dashed line in FIG. 4B (i.e., 404*g*→404*h*→404*f*→404*a*→404*e*→404*b*→404*d*→404*c*), so that the respective feedback contacts produce the temperature change in the order under an action of the driving electrical signal. Thus, the smart wristband 402 accordingly outputs the temperature signal in a direction from the feedback contact 404*g* to the feedback contact 404*c* (as shown by an arrow 410) to the user.

For example, as shown in FIG. 4C, the feedback contact 404*a* and the feedback contact 404*e* are respectively a leftmost feedback contact and a rightmost feedback contact. When the suggested moving direction provided to the user is about 45 degrees right front, the controller may sequentially apply a driving electrical signal to the feedback contacts 404*h*, 404*a*, 404*g*, 404*b*, 404*f*, 404*c*, 404*e* and 404*d* according to an order shown by a dashed line in FIG. 4C (i.e., 404*h*→404*a*→404*g*→404*b*→404*f*→404*c*→404*e*→

404*d*), so that the respective feedback contacts produce the temperature change in this order under an action of the driving electrical signal. Thus, the smart wristband 402 accordingly outputs the temperature signal in a direction from the feedback contact 404*h* to the feedback contact 404*d* (as shown by an arrow 412) to the user.

Figure 5:
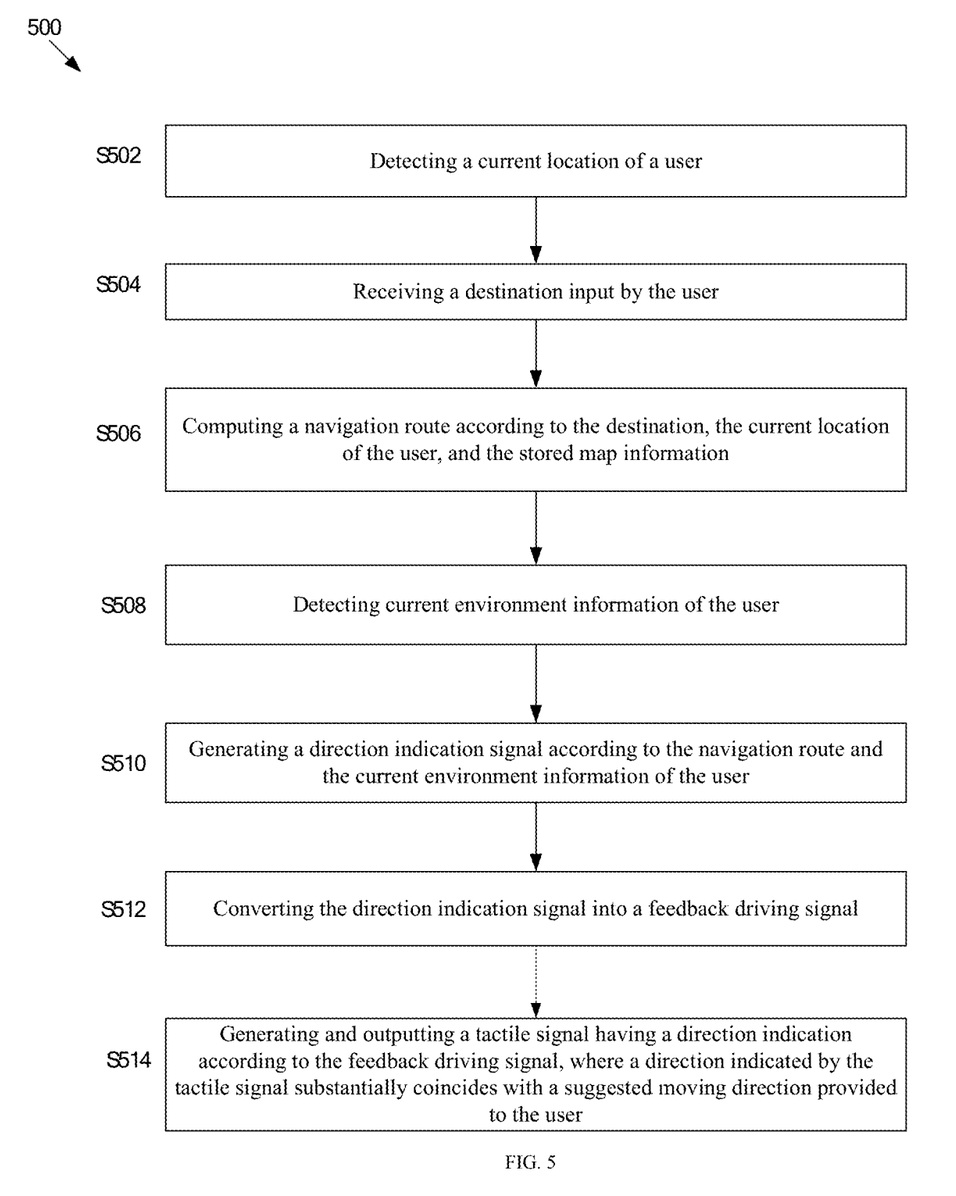
FIG. 5 is a flow chart of an example wearable tactile navigation method provided by an embodiment of the present disclosure.

FIG. 5 is a flow chart of a wearable tactile navigation method 500 provided by an embodiment of the present disclosure. The wearable tactile navigation method 500 may be executed by the wearable tactile navigation device provided by embodiments of the present disclosure, or may be executed by other navigation devices. The wearable tactile navigation method 500 may comprise steps S502, S504, S506, S508, S510, S512 and S514, or may also comprise other methods or steps executed by the wearable tactile navigation device provided by the embodiments of the present disclosure. Repeated description will not be provided here. As an example, the method 500 will be described below in conjunction with FIG. 1A and FIG. 1B.

In step S502, the method 500 may detect a current location of a user. For example, a locator 104 may detect the current location of the user. In step S504, the method 500 may receive a destination input by the user. For example, the user may input destination information through an inputter 106.

In step S506, the method 500 may compute a navigation route according to the destination, the current location of the user, and the map information acquired (stored or downloaded). For example, the processor 108 may compute the navigation route according to the destination, the current location of the user, and the stored map information.

In step S508, the method 500 may detect current environment information of the user. For example, the environment detector 122 may detect current traffic information of the user.

In step S510, the method 500 may generate direction indication information according to the navigation route and the current environment information of the user. For example, the processor 108 may generate the direction indication information according to the navigation route and the current environment information of the user.

In step S512, the method 500 may convert the direction indication signal into a feedback driving signal. For example, the controller 124 may receive the direction indication signal from the processor 108, and convert the direction indication signal into the feedback driving signal.

In step S514, the method 500 may generate and output a directional tactile signal according to the feedback driving signal, where a direction indicated by the tactile signal substantially coincides with a suggested moving direction provided to the user. For example, the tactile navigation actuator 126 may generate and output the directional tactile signal according to the feedback driving signal. The tactile signal includes at least one of a force signal, a temperature signal, and an electrical signal. A size of the tactile signal changes according to an indication urgency degree of the direction indication signal.

For example, a force feedback implementation mode of the force signal of the tactile signal applied at a single feedback contact includes vibrating, tapping, or pressing.

For example, the generating and outputting a directional tactile signal according to the feedback driving signal, includes: sequentially applying the electrical signal in a certain order to the feedback contacts according to the feedback driving signal of the tactile navigation actuator, so as to generate a temperature signal of the tactile signal, where each feedback contact includes a material that produces a temperature change according to a size of the applied electrical signal.

It can be understood that, in embodiments of the present disclosure, the user of the wearable tactile navigation device may be a receiver of the tactile signal, and the receiver performs navigation with the received tactile signal.

FIG. 6A to FIG. 6B show an example of updating setting of action regions corresponding to feedback points. For example, the wearable tactile navigation device 602 is a wearable smart wristband, the smart wristband is provided thereon with an orientation detecting point, and a main trunk of the body of the user serves as an orientation reference point. The orientation detecting point may be any point on the wristband, for example, a feedback contact 606*a* or another feedback contact. FIG. 6A shows an initial state when the wristband is worn. A motion sensor may sense initial orientation information of the orientation detecting point with respect to the orientation reference point in the initial state. The motion sensor may include a multi-axis accelerometer, a multi-axis magnetometer, or a multi-axis gyroscope. In the setting of the action regions corresponding to the feedback points in the initial state, feedback contacts corresponding to a straight front direction, a straight back direction, a left side, and a right side of the user are respectively 606*c*, 606*g*, 606*a* and 606*e*.

When the arm of the user is twisting, the motion sensor may sense change in the orientation information of the orientation detecting point with respect to the orientation reference point, and then the controller 124 may correct or update the setting of the active regions corresponding to the feedback points according to the change of the orientation information. For example, as shown in FIG. 6B, when the arm of the user twists 45 degrees to the right, the motion sensor senses that the change of the orientation information of the orientation detecting point with respect to the orientation reference point is twisting 45 degrees to the right, and thus, the controller 124 may change the feedback setting as the following: the feedback contacts corresponding to the straight front direction, the straight back direction, the left side, and the right side of the user are respectively 606*a*, 606*e*, 606*c*, and 606*g*.

Hereinbefore, the wearable tactile navigation device and method provided by the embodiments of the present disclosure are described with reference to FIG. 1A and FIG. 1B to FIG. 6B, which can provide the user (e.g., a visually impaired person) with the directional tactile navigation signal, so as to provide a more direct navigation advice than the voice prompt and other navigation information.

It should be noted that in the present disclosure terms such as "first", "second" and the like used in the present disclosure do not indicate any sequence, quantity or significance but only for distinguishing different constituent parts. Also, the terms such as "a," "an," or "the" etc., are not intended to limit the amount, but indicate the existence of at lease one. The terms "comprises," "comprising," "includes," "including," etc., are intended to specify that the elements or the objects stated before these terms encompass the elements or the objects and equivalents thereof listed after these terms, but do not preclude the other elements or objects.

Finally, it should be explained that a series of processes above comprise the processes carried out according to the time sequence as described herein, and the processes carried out in parallel or separately, not in accordance with the time sequence.

Through the above description of the implementations, a person skilled in the art can clearly know that the present disclosure can be implemented by a software plus necessary hardware platform. Of course, it can also be wholly executed by the hardware.

What are described above is related to the illustrative embodiments of the disclosure only and not limitative to the scope of the disclosure; any changes or replacements easily for those technical personnel who are familiar with this technology in the field to envisage in the scopes of the disclosure, should be in the scope of protection of the present disclosure. Therefore, the scopes of the disclosure are defined by the accompanying claims.

The present application claims the priority of the Chinese Patent Application No. 201610345176.X filed on May 23, 2016, which is incorporated herein by reference in its entirety as part of the disclosure of the present application.

The invention claimed is:

1. A wearable tactile navigation device, comprising:
   a tactile navigation actuator, comprising a plurality of feedback contacts and configured to control the at least one feedback contact based on a direction indication signal to generate a tactile signal having a direction indication, wherein a direction indicated by the tactile signal substantially coincides with a suggested moving direction provided to a user of the wearable tactile navigation device, and each feedback contact corresponds to a direction indication action region;
   wherein the wearable tactile navigation device further comprises a motion sensor, wherein one of the plurality of feedback contacts is used as an orientation detecting point, the motion sensor is configured to sense change in orientation information of the orientation detecting point with respect to a body of the user, and the change in the orientation information of the orientation detecting point with respect to the body of the user is used to change the direction indication action region corresponding to each feedback contact.

2. The wearable tactile navigation device according to claim 1, wherein the tactile navigation actuator sequentially controls the plurality of feedback contacts in a certain order to generate the tactile signal based on the direction indication signal.

3. The wearable tactile navigation device according to claim 1, wherein a size of the tactile signal changes based on an indication urgency degree of the direction indication signal.

4. The wearable tactile navigation device according to claim 1, wherein the tactile signal includes at least one of a force signal, a temperature signal, and an electrical signal.

5. The wearable tactile navigation device according to claim 1, wherein the tactile signal includes a force signal, and an implementation mode in which the at least one feedback contact generates the force signal includes vibrating, tapping or pressing.

6. The wearable tactile navigation device according to claim 1, wherein the wearable tactile navigation device comprises a wearable vest, a wristband, an arm band, a knee pad, a belt, a headband, a glove or a hat.

7. The wearable tactile navigation device according to claim 1, wherein the wearable tactile navigation device is a wearable vest, and the at least one feedback contact includes a first feedback contact located at a left shoulder of the vest and a second feedback contact located at a right shoulder of the vest, and
   a direction indication action region corresponding to the first feedback contact is a left half of a body of the user, and a direction indication action region corresponding to the second feedback contact is a right half of the body of the user.

8. The wearable tactile navigation device according to claim 1, further comprising:
   an environment detector, configured to detect current environment information of the user;
   a locator, configured to detect a current location of the user and to acquire map information;
   an inputter, configured to receive destination information input by the user; and
   a processor, configured to compute a navigation route based on the destination, the current location of the user and the map information, and to generate the direction indication signal based on the navigation route and the current environment information of the user detected by the environment detector.

9. The wearable tactile navigation device according to claim 8, wherein the processor is further configured to:
   determine a direction toward which the user substantially faces after moving based on a location before and a location after the user moves toward a certain direction; or
   determine a current direction toward which the user approximately faces based on different orientations of two or more feedback contacts provided in the tactile navigation actuator.

10. The wearable tactile navigation device according to claim 1, wherein the motion sensor is configured to detect a twisting direction of the tactile navigation actuator, and the twisting direction of the tactile navigation actuator is used for assisting generation of the direction indication signal.

11. The wearable tactile navigation device according to claim 1, wherein an angle by which the direction indication action region corresponding to each feedback contact is changed is equal to a rotation angle of the orientation detecting point with respect to the body of the user.

12. The wearable tactile navigation device according to claim 1, wherein
   the wearable tactile navigation device comprises a wristband,
   the plurality of feedback contacts comprises a first feedback contact, a second feedback contact, a third feedback contact and a fourth feedback contact, the first feedback contact corresponds to a straight front direction of the user, the second feedback contact corresponds to a straight back direction of the user, the third feedback contact corresponds to a left side of the user and the fourth feedback contact corresponds to a right side of the user, and
   in a case where an arm of the user wearing the wristband twists 45 degrees rightward, the motion sensor senses that the orientation detecting point is twisted 45 degrees rightward with respect to the body of the user, and the first feedback contact is changed to correspond to the right side of the user, the second feedback contact is changed to correspond to the left side of the user, the third feedback contact is changed to correspond to the straight front direction of the user and the fourth feedback contact is changed to correspond to the straight back direction of the user.

13. A wearable tactile navigation method, comprising:
   receiving a direction indication signal; and
   generating, by a plurality of feedback contacts, a tactile signal having a direction indication based on the direction indication signal, wherein a direction indicated by the tactile signal substantially coincides with a suggested moving direction provided to a receiver of the tactile signal; and sensing change in orientation information of an orientation detecting point with respect to a body of the receiver, wherein one of the plurality of feedback contacts is used as the orientation detecting point, the change in the orientation information of the orientation detecting point with respect to the body of the receive is used to change a direction indication action region corresponding to each feedback contact.

14. The wearable tactile navigation method according to claim 13, wherein a size of the tactile signal changes based on an indication urgency degree of the direction indication signal.

15. The wearable tactile navigation method according to claim 13, further comprising:
acquiring current map information;
detecting a current location of the receiver of the tactile signal;
receiving a destination input by the receiver of the tactile signal;
computing a navigation route based on the destination, the current location of the receiver of the tactile signal, and the acquired map information;
detecting current environment information of the receiver of the tactile signal; and
generating the direction indication signal based on the navigation route and the current environment information of the receiver of the tactile signal.

16. The wearable tactile navigation method according to claim 13, wherein the tactile signal includes a plurality of tactile sub-signals, each tactile sub-signal corresponds to a direction indication action region;
the tactile sub-signals are sequentially generated in a certain order based on the direction indicated by the tactile signal.

17. The wearable tactile navigation method according to claim 13, further comprising: determining a current direction toward which the receiver of the tactile signal substantially faces, including:
determining the current direction toward which the receiver of the tactile signal substantially faces based on a location before and a location after the receiver of the tactile signal moves toward a certain direction; or
determining the current direction toward which the receiver of the tactile signal substantially faces based on different locations of two or more direction indication action regions.

18. The wearable tactile navigation method according to claim 13, further comprising: detecting a twisting direction of a direction indication action region with respect to the current direction toward which the receiver of the tactile signal substantially faces, the twisting direction being used for assisting generation of the direction indication signal.

19. The wearable tactile navigation method according to claim 13, wherein an angle by which the direction indication action region corresponding to each feedback contact is changed is equal to a rotation angle of the orientation detecting point with respect to the body of the receiver.

20. The wearable tactile navigation method according to claim 13, wherein
the plurality of feedback contacts comprises a first feedback contact, a second feedback contact, a third feedback contact and a fourth feedback contact, the first feedback contact corresponds to a straight front direction of the receiver, the second feedback contact corresponds to a straight back direction of the receiver, the third feedback contact corresponds to a left side of the receiver and the fourth feedback contact corresponds to a right side of the receiver,
the sensing the change in orientation information of the orientation detecting point with respect to the body of the receiver comprises:
sensing that the orientation detecting point is twisted 45 degrees rightward with respect to the body of the receiver, and
changing the first feedback contact to correspond to the right side of the receiver, changing the second feedback contact to correspond to the left side of the receiver, changing the third feedback contact to correspond to the straight front direction of the receiver and changing the fourth feedback contact to correspond to the straight back direction of the receiver.

* * * * *